United States Patent
Proietti et al.

(10) Patent No.: US 7,833,803 B2
(45) Date of Patent: Nov. 16, 2010

(54) ANALYSIS OF LIQUID CHROMATOGRAPHY ELUATES

(75) Inventors: Daniela Proietti, Siena (IT); Angela Bardotti, Siena (IT); Stefano Ricci, Siena (IT)

(73) Assignee: Novartis AG, Basel (CH)

( * ) Notice: Subject to any disclaimer, the term of this patent is extended or adjusted under 35 U.S.C. 154(b) by 586 days.

(21) Appl. No.: 11/597,254

(22) PCT Filed: May 20, 2005

(86) PCT No.: PCT/IB2005/001772
§ 371 (c)(1),
(2), (4) Date: Nov. 1, 2007

(87) PCT Pub. No.: WO2005/114171
PCT Pub. Date: Dec. 1, 2005

(65) Prior Publication Data
US 2008/0258710 A1   Oct. 23, 2008

(30) Foreign Application Priority Data
May 20, 2004   (GB) ................. 0411283.5
Sep. 16, 2004  (GB) ................. 0420649.6

(51) Int. Cl.
*G01N 25/08* (2006.01)
*G01N 30/02* (2006.01)
(52) U.S. Cl. ............ 436/161; 436/164; 356/319; 356/326; 422/70
(58) Field of Classification Search ............ 436/161
See application file for complete search history.

(56) References Cited

U.S. PATENT DOCUMENTS 4,727,034 A  * 2/1988  Matsushita et al. .......... 436/161
6,008,036 A  * 12/1999 Fanget et al. ................ 435/239
2003/0062475 A1  4/2003  Karst et al.

FOREIGN PATENT DOCUMENTS

JP      11051922 A     2/1999

OTHER PUBLICATIONS

C.L.F. Meyers, 2000, Current Protocols in Nucleic Acid Chemistry, Chromatography, John Wiley & Sons Inc., A.3E.1-A.3E.7.*
Talaga, P., Vialle, S., Moreau, M.; Development of a high-performance anion-exchange chromatography with pulsed-amperometric detection based quantification assay for pneumococcal polysaccharides and conjugates, 2002, Vaccine, 20, pp. 2474-2484.*

(Continued)

*Primary Examiner*—Krishnan S Menon
*Assistant Examiner*—Allison Gionta
(74) *Attorney, Agent, or Firm*—Helen Lee; Otis Littlefield (57) ABSTRACT

When analysing saccharides by HPAEC, the eluate from the column is typically analysed using a amperometric detector. According to the invention, amperometric detection is coupled with ultraviolet detection, with both methods being applied to the eluate. Thus the invention provides a method for analysing the eluate from a liquid chromatography column, wherein the eluate is analysed by both (a) amperometric detection and (b) ultraviolet detection. The information content derivable from using both sorts of detection advantageously exceeds that derivable from either of the two detection methods alone.

10 Claims, 9 Drawing Sheets

OTHER PUBLICATIONS

Dionex, CarboPac PA1 and PA10 Columns for Mono- and Disaccharide Analysis.*

Kesler, R. B., Rapid Quantitative Anion-Exchange Chromatography of Carbohydrates, 1967, Analytical Chemistry, 39 (12), pp. 1416-1422.*

Ricci et al., Development of a new method fro the quantitative analysis of the extracellular polysaccharide of *Neisseria meningitidis* serogroup A by use of high-performance anion-exchange chromatography with pulsed-amperometric detection, 2001, Vaccine, 1989-1997.*

Dionex AS11 Hyroxide-Selective Anion-Exchange Column, http://www.dionex.com/en-us/products/columns/ic-rfic/hydroxide-selective/ionpac-as11/lp-73256.html, accessed Dec. 15, 2009.*

Dionex, Analysis of Carbohydrates by High Performance Anion Exchange Chromatography with Pulsed Amperometric Detection (HPAE-PAD), 2000, Technical Note 20.*

Ricci et al., Development of a new method for the quantitative analysis of the extracellular polysaccharide of *Neisseria meningitidis* serogroup A by use of high-performance anion-exchange chromatography with pulsed-amperometric detection.*

Patent Abstracts of Japan, 1999(5), May 31, 1999 & JP 11 051922 Feb. 26, 1999.

Kotani N. et al. "Analysis of 2-aminobenzamide-labeled oligosaccharides by high pH anion-exchange chromatography with.. " Analytical Biochemistry, 264(1): 66-73 (1998).

Obrezkov, O. et al. "Ion chromatographic determination of anions, especially sulphur-containing anions, with conductimetric . . . " Journal of Chromatography, 558: 209-213 (1991).

Cataldi, T. et al. "Carbohydrate analysis by high-performance anion-exchange chromatography with pulsed . . . " Fresenius J of Anal Chem, 368(8): 739-758 (2000).

Bardotti, A. et al. "Quantitative determination of saccharide in *Haemophilus influenzae* type b glycoconjugate vaccines, alone and in . . . " Vaccine, 18: 1982-1993 (2000).

* cited by examiner

ANALYSIS OF LIQUID CHROMATOGRAPHY ELUATES

RELATED APPLICATIONS

This application is the U.S. National Phase of International Application No. PCT/IB32005/001772, filed May 20, 2005 and published in English, which claims priority to Great Britain Application No. 0411283.5, filed May 20, 2004, and Great Britain Application No. 0420649.6, filed Sep. 16, 2004. The teachings of the above applications are incorporated herein in their entirety by reference.

All documents cited herein are incorporated by reference in their entirety.

TECHNICAL FIELD

This invention is in the field of analysis of saccharides.

BACKGROUND ART

Immunogens comprising capsular saccharide antigens conjugated to carrier proteins are well known in the art. Conjugation converts T-independent antigens into T-dependent antigens, thereby enhancing memory responses and allowing protective immunity to develop, and the prototype conjugate vaccine was for *Haemophilus influenzae* type b (Hib) [e.g. see chapter 14 of ref. 1]. Since the Hib vaccine, conjugated saccharide vaccines for protecting against *Neisseria meningitidis* (meningococcus) and against *Streptococcus pneunioniae* (pneumococcus) have been developed. Other organisms where conjugate vaccines are of interest are *Streptococcus agalactiae* (group B streptococcus), *Pseudomonas aeruginosa* and *Staphylococcus aureus*.

Where saccharides are included in vaccines and other biological products then regulatory authorities generally require their characterisation. A common technique used for saccharide characterisation is anion chromatography, and in particular high performance anion exchange chromatography (HPAEC), usually with pulsed amperometric detection (PAD) [2,3]. Suitable HPAEC-PAD systems are provided by Dionex™ Corporation (Sunnyvale, Calif.) e.g. the BioLC™ system. These systems can quantitatively analyse individual saccharides within mixtures without the need for derivatisation or pre-analysis separation, and analysis of mixed saccharides can be used in saccharide profiling.

When analysing saccharides, the eluate from a HPAEC column is typically analysed using a pulsed amperometric detector (PAD) i.e. detection is based on electrical current. At suitable (high) pH, carbohydrates can be electrocatalytically oxidised at the surface of electrodes by applying a positive potential. The current generated is this way is proportional to the carbohydrate concentration, allowing detection and quantification of the carbohydrate by amperometry. Compared with simple amperometric detection, the PAD technique intersperses short pulses of a cleaning and regeneration potential with the standard detecting potential, thereby avoiding difficulties that arise when oxidation products of analytes foul the electrodes. As well as being used for HPAEC analysis, PAD is also used for analysing HP cation-exchange chromatography [4] and other HPLC separations.

To obtain further analytical information, particularly when dealing with compounds that are not amperometrically active and with chemically-modified compounds, the inventors decided to analyse eluates by spectroscopic means. Unfortunately, the high pH used during HPAEC analysis of capsular saccharides means that hydroxide ions are present in the eluate, and the high absorbance of these ions (particularly in the ultraviolet region) meant that addition of spectroscopic analysis was not easy. Hydroxide ions could be removed by using a micro-membrane chemical suppressor device, but this introduced new problems, as the acetate typically used as a 'pushing agent' for eluting capsular saccharides is converted by the suppressor into highly absorbent acetic acid.

It is an object of the invention to provide further and improved methods and systems for performing anion chromatography characterisation of saccharides. In particular, it is an object to overcome the difficulties in spectroscopic analysis of eluates that arise from the presence of either hydroxide ions or, after conversion of hydroxide ions, acetic acid.

DISCLOSURE OF THE INVENTION

To overcome these difficulties caused by using hydroxide/acetate-based eluents, the inventors used two approaches. First, they chose to use weaker anion exchange supports that do not require an acetate pushing agent. Such columns are not currently used for analysing carbohydrates, but are more typically used for resolving a large number of inorganic and organic acid anions [5]. Second, they chose to use pushing agents with low spectroscopic absorbance. Both of these approaches allowed spectroscopic detection to be combined with PAD detection. Moreover, they were also compatible with normal HPAEC-PAD protocols and they can advantageously be used even where spectroscopic detection is not desired, particularly as they permit better resolution of long oligosaccharides.

According to a first aspect of the invention, therefore, amperometric detection is coupled with spectroscopic detection, such that both detection methods are used. Thus the invention provides a method for analysing the eluate from a liquid chromatography column, wherein the eluate is analysed by both amperometry and spectroscopy. The invention also provides an apparatus for analysing a sample, wherein the apparatus comprises (i) a liquid chromatography column, (ii) an amperometric detector and (iii) a spectroscopic detector, wherein the two detectors are arranged to receive eluate from the column.

Figure 1:
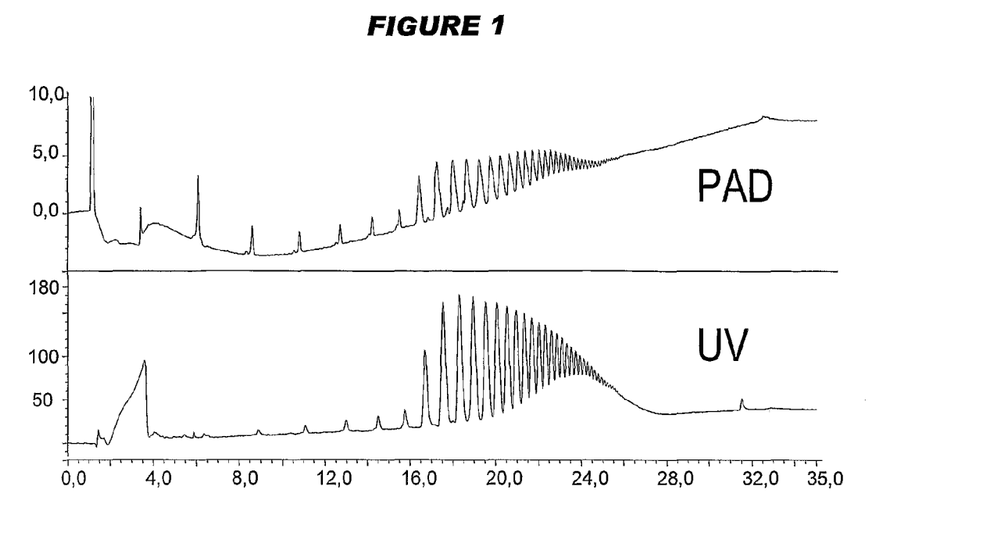
FIG. 1 shows the output from an HPAEC analysed serially by amperometric means (upper profile) and by $UV_{200nm}$ spectroscopy (bottom profile). The units of measurement in the upper profile are nC; the lower profile uses arbitrary units.

The separate use of PAD or UV detection for analysing the output of HPAEC columns has been reported [6], but the use of both amperometric and spectroscopic techniques for analysing the same eluate is new. The information content derivable from using both sorts of detection advantageously exceeds that derivable from either of the two detection methods alone e.g. as seen in FIG. 1, some peaks give better dynamic range in UV than PAD, and some peaks are better in PAD than in UV.

In a second aspect, the invention also provides a method for eluting a capsular saccharide analyte from an anion exchange chromatography column, wherein the analyte is eluted using an eluent comprising an anion other than an acetate or a hydroxide. The eluent preferably comprises an anion selected from the group consisting of: a nitrate; a chloride; a carbonate; and a borate. Sodium salts of these anions can conveniently be used. This method is particularly useful when the eluent is basic (e.g. pH>9), even more so if a chemical suppressor of hydroxide ions is being used, and provides better resolution of long oligosaccharides. Moreover, this method is particularly useful for analysis of acetylated saccharides.

In a third aspect, the invention also provides a method for analysing a saccharide by anion exchange chromatography, wherein the chromatography is performed using a column that has a capacity of less than 50 µeq (e.g. $\leq$40 µeq, $\leq$30 µeq, $\leq$20 µeq, etc.). The use of a low capacity column means that elution is rapid and pushing agents do not need to be used. Hydroxide suppression can thus be used without generating acetic acid. An acetate-free hydroxide eluent will typically be used, and the avoidance of acetate ions is particularly useful for analysis of acetylated saccharides. The low capacity columns allow better resolution of long oligosaccharides.

The second and third aspects of the invention can advantageously be used together i.e. the invention provides a method for analysing a capsular saccharide analyte by anion exchange chromatography, wherein the chromatography is performed using a column that has a capacity of less than 50 µeq, and wherein elution from the column uses an eluent comprising an ion selected from the group consisting of a nitrate and a chloride.

The invention also provides the eluate of a chromatographic method of the invention. The invention further provides a pharmaceutical comprising as an active ingredient a substance that has been analysed using a method of the invention. In particular, the invention provides an immunogenic composition, such as a vaccine, comprising a bacterial capsular saccharide that has been analysed using a method of the invention.

The Liquid Chromatography Column

The first aspect of the invention is useful for analysing the output from a liquid chromatography column. This aspect can be applied to various liquid chromatography columns, but it is preferably used with high performance liquid chromatography (HPLC). The invention is particularly useful for analysing the results of separation by high performance anion exchange chromatography (HPAEC) or by high performance cation exchange chromatography (HPCEC).

Preferred columns are those that spontaneously retain saccharides such that the saccharides have to be eluted from the column. Elution from the chromatography column can be an isocratic elution or a gradient elution. Eluents including sodium hydroxide and/or sodium acetate are typical eluents used during HPAEC-PAD analysis of saccharides. In the second aspect of the invention, however, nitrate and/or chloride salt eluents (typically sodium salts) are used, usually substantially in the absence of any acetate eluent. For eluting analytes from anion exchange columns then the eluent will generally be basic e.g. the pH will be >8, >9, >10, >11, >12, >13, etc. Hydroxide salts (e.g. NaOH) can be used to achieve the desired pH, and hydroxide ions are typical for use in anion exchange eluents.

Eluates may be subjected to chemical suppression of hydroxide ions, particularly where the ions interfere with an analytical detection technique that is being used. A micromembrane suppressor can conveniently be used, such as the MMS products from Dionex™. The 'MMS III' product uses continuous chemical suppression to enhance analyte conductivities while decreasing eluent conductivity, and enables direct conductivity detection with ion-exchange applications using isocratic or gradient elution over wide concentration ranges. Suppressors that generate acetic acid from acetate ions are preferably avoided when acetate ions are included in the eluent and the generated acetic acid interferes with an analytical detection technique that is being used.

Preferred HPAEC columns for use with the first and second aspects of the invention are the "CarboPac" columns marketed by Dionex, such as the PA1 [10 µm diameter polystyrene substrate 2% crosslinked with divinylbenzene, agglomerated with 500 nm MicroBead quaternary ammonium functionalized latex (5% crosslinked)], PA100, PA20, PA10 [10 µm diameter ethylvinylbenzene substrate 55% crosslinked with divinylbenzene, agglomerated with 460 nm MicroBead difunctional quaternary ammonium ion (5% crosslinked)], PA200 or MA1 columns. Preferred HPCEC columns are the "IonPac" columns also marketed by Dionex, including the CS10 column.

As an alternative to using liquid chromatography, the first aspect of the invention can be used to analyse the output of a capillary electrophoresis separation e.g. the Beckman-Coulter P/ACE system.

For the third aspect of the invention, the anion exchange column has an ion capacity of less than 50 µeq (milliequivalents of charge) e.g. <40 µeq, <30 µeq, <20 µeq, etc. Preferred HPAEC columns are the hydroxide-selective "IonPac AS" columns marketed by Dionex, such as the AS11 column, with alkanol quaternary ammonium functional groups. When used in its 2×250 mm analytical format, the AS11 column has a capacity of 11 µeq, which increases to 45 µeq when used in a 4×250 mm format. Low capacity hydroxide-selective columns are preferred.

Amperometric and Spectroscopic Detection

Figure 2:
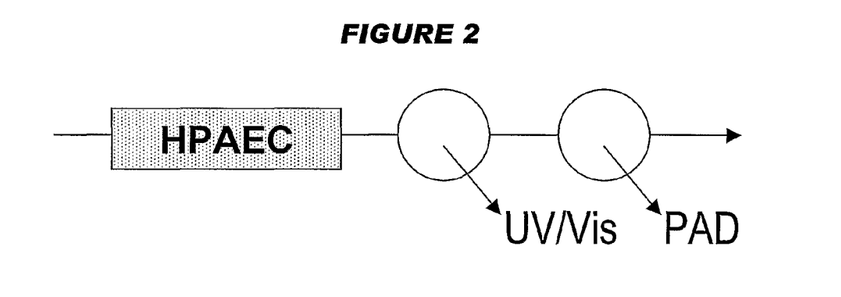
Figure 3:
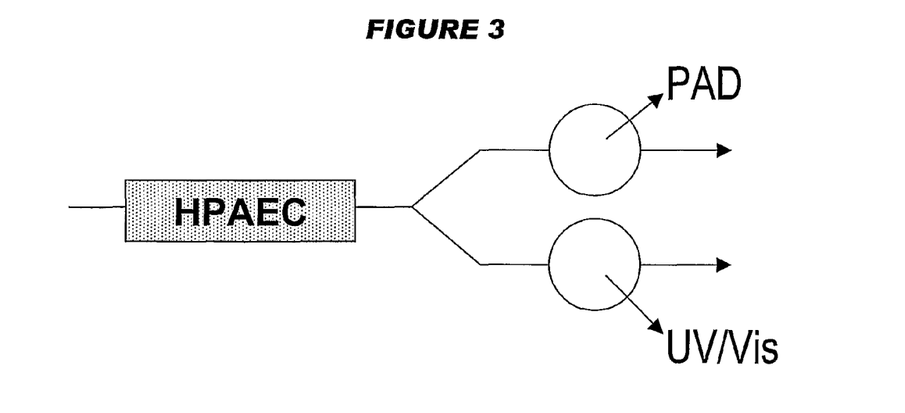
FIG. 3 shows a parallel arrangement.

The first aspect of the invention analyses the eluate of a liquid chromatography column both amperometrically and spectroscopically. Material eluting from a column can be split, with one portion being analysed amperometrically and another portion being analysed spectroscopically. As an alternative, material eluting from a column can be analysed in series without splitting, either amperometrically then spectroscopically or spectroscopically then amperometrically. These two different general methods are illustrated in FIGS. 2 & 3. Where serial analysis is used then it may be preferred to perform spectroscopic detection before amperometric detection, particularly if the spectroscopic detection is non-destructive relative to the amperometric detection.

Figure 4A:
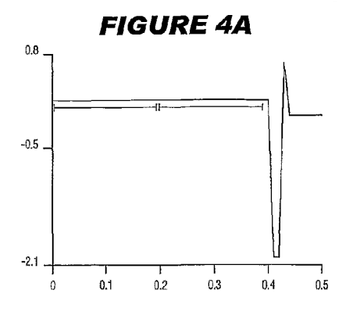
FIG. 4 shows three PAD waveforms. The x-axis shows time in seconds. The y-axis shows potential in volts, relative to an Ag/AgCl reference electrode. All three waveforms have a delay period (first bar), a detection period (second bar), and then a cleaning period.
Figure 4B:
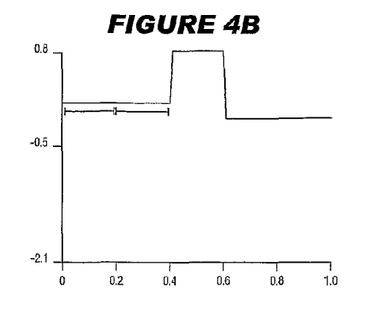
Figure 4C:
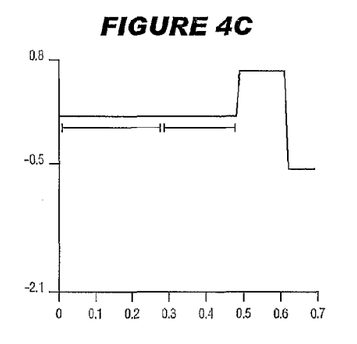

The amperometric detection is preferably a pulsed amperometric detection (PAD). Various waveforms can be used in PAD [7], including any of those with the profiles shown in FIG. 4. The use of a negative potential for cleaning the electrode is preferred. The FIG. 4A waveform uses a negative potential for electrode cleaning, and both improves long term reproducibility and reduces electrode wear.

The electrode used for the amperometric detection is preferably a gold electrode.

The spectroscopic detection is preferably based on the absorption and/or emission of electromagnetic radiation, preferably with a wavelength between 100 nm and 900 nm (e.g. with a wavelength in the range 100-200 nm, 150-250 nm, 200-300 nm n 250-350 nm, 300-400 nm, 350-450 nm, 400-500 nm, 450-550 nm, 500-600 nm, 550-650 nm, 600-700 nm, 650-750 nm, 700-800 nm, 750-850 nm, 800-900 nm). The wavelength of light used can be selected according to the analyte(s) to be detected. Ultraviolet (UV) absorption spectroscopy (e.g. at 200 nm) and visible light absorption spectroscopy are two particularly preferred methods for analysing saccharides.

As an alternative to using amperometric detection, the invention may use conductivity detection (including suppressed conductivity detection).

Analytes

The invention is used to analyse the eluate from a liquid chromatography column. The eluate will be the result of chromatographic separation of one or more analytes in a sample.

The invention is particularly useful for analysing saccharide analytes. These may be polysaccharides (e.g. with a degree of polymerisation of at least 10, e.g. 20, 30, 40, 50, 60 or more), oligosaccharides (e.g. with a degree of polymerisation of from 2 to 10), or monosaccharides. Oligosaccharides and monosaccharides may be the result of depolymerisation and/or hydrolysis of a parent polysaccharide e.g. the analyte may be a saccharide-containing fragment of a larger saccharide.

Preferred saccharide analytes are bacterial saccharides, and particularly bacterial capsular saccharides e.g. from *Neisseria meningitidis* (serogroups A, B, C, W135 or Y), *Streptococcus pneumoniae* (serotypes 4, 6B, 9V, 14, 18C, 19F, or 23F), *Streptococcus agalactiae* (types Ia, Ib, II, III, IV, V, VI, VII, or VIII), *Haemophilus influenzae* (typeable strains: a, b, c, d, e or f), *Pseudomonas aeruginosa, Staphylococcus aureus*, etc. Other saccharide analytes include glucans (e.g. fungal glucans, such as those in *Candida albicans*), and fungal capsular saccharides e.g. from the capsule of *Cryptococcus neoformans*.

The *N. meningitidis* serogroup A capsule is a homopolymer of (α1→6)-linked N-acetyl-D-mannosamine-1-phosphate. The *N. meningitidis* serogroup B capsule is a homopolymer of (α 2→8) linked sialic acids. The *N. meningitidis* serogroup C capsular saccharide is a homopolymer of (α 2→9) linked sialic acid. The *N. meningitidis* serogroup W135 saccharide is a polymer consisting of sialic acid-galactose disaccharide units [→4)-D-Neup5Ac(7/9OAc)-α-(2→6)-D-Gal-α-(1→]. The *N. meningitidis* serogroup Y saccharide is similar to the serogroup W135 saccharide, except that the disaccharide repeating unit includes glucose instead of galactose [→4)-D-Neup5Ac(7/9OAc)-α-(2→6)-D-Glc-α-(1→]. The *H. influenzae* type b capsular saccharide is a polymer of ribose, ribitol, and phosphate ['PRP', (poly-3-β-D-ribose-(1, 1)-D-ribitol-5-phosphate)].

In addition to being useful for analysing full-length capsular saccharides, the invention can be used with oligosaccharide fragments of them.

Other preferred saccharide antigens are those cleaved from glycoconjugates e.g. from saccharide-protein conjugate vaccine antigens. Of the three *N. meningitidis* serogroup C conjugated vaccines that have been approved for human use, Menjugate™ [8] and Meningitec™ are based on oligosaccharides, whereas NeisVac-C™ uses full-length polysaccharide.

Other preferred saccharide antigens are eukaryotic saccharides e.g. fungal saccharides, plant saccharides, human saccharides (e.g. cancer antigens), etc.

Saccharides that are charged (e.g. anionic) at neutral pH are preferred analytes. Saccharide analytes with multiple phosphate and/or multiple carboxylate groups can be analysed using the methods of the invention. The invention is thus particularly useful for analysing polyanionic saccharide analytes.

Other preferred analytes are lipopolysaccharides and lipooligosaccharides.

The invention is particularly useful for use with analytes that include various saccharides of different lengths e.g. different fragments of the same parent saccharide.

The analyte will generally be in aqueous solution, and this solution will have a high pH and high salt concentration, as a result of HPAEC.

Typical analytes are those that can be detected by both amperometric and spectroscopic techniques.

As well as containing analyte(s) of interest, samples to be analysed can include other materials. These may or may not be retained by the chromatography column, and so may or may not be present in the eluate. Typically such components will not bind to the column.

Thus the eluates analysed by the methods of the invention will include these analytes or will be suspected of including them.

The analyte may be a product to be tested prior to release (e.g. during manufacture or quality control testing), or may be a product to be tested after release (e.g. to assess stability, shelf-life, etc.).

Further Steps

Prior to analysing the eluate from a liquid chromatography column, the method of the invention may involve adding an analyte-containing sample (or suspected of containing an analyte) to the column. Thus the invention provides a method for detecting the presence of an analyte in a sample, comprising the steps of: (a) applying the sample to a liquid chromatography column, such that analyte in the sample is retained by the column; (b) eluting the analyte from the column; and (c) analysing the eluate as described above.

For saccharide analysis, it may be desired to filter at least some non-analyte compounds from the sample before entry to the column, and Dionex™ produce pre-column traps and guards for this purpose e.g. an amino trap for removing amino acids, a borate trap, etc.

After elution and analysis, the invention may include the further step of determining a characteristic of a detected analyte e.g. its DP (typically an average DP), its molecular weight, its purity, etc.

After the amperometric and spectroscopic detectors, the eluate may be coupled into a mass spectrometer e.g. FAB/MS or ESI/MS.

Use of the Invention to Select Desired Saccharides

The invention is particularly useful prior to conjugation at a stage where it is necessary to ensure that correctly-sized saccharide chains are selected for production of a conjugate.

The invention allows the progress of fragmentation of a full-length polysaccharide prior to conjugation to be checked or monitored. Where oligosaccharides of a particular length (or range of lengths) are desired then it is important that fragmentation of the polysaccharide should not be so extensive as to take depolymerisation past the desired point (e.g. at the extreme, to give monosaccharides). The invention allows the progress of this partial depolymerisation to be monitored, by measuring saccharide chain length over time. Thus the invention provides a process for analysing saccharide(s) in a composition, comprising the steps of: (a) starting depolymerisation of the saccharide(s) in the composition; and, at one or more time points thereafter, (b) analysing the saccharide(s) as described herein. In an initial run of experiments then it will be usual to analyse at several time points in order to determine progress over time, but after standard conditions have been established then it be usual to analyse at a set time point for confirmatory purposes. Once a desired end-point has been reached then the process may comprise the further step of: (c) stopping the depolymerisation, e.g. by washing, separating, cooling, etc. The process may also comprise the further step of conjugation of the depolymerised saccharide to a carrier protein, after optional chemical activation.

The invention also allows selection of desired oligosaccharide chains after fragmentation. Thus the invention provides a process for selecting saccharides for use in preparing a glycoconjugate, comprising the steps of: (a) obtaining a composition comprising a mixture of different polysaccharide fragments; (b) separating the mixture into sub-mixtures; (c) analysing one or more sub-mixtures using a process as described herein; and (d) using the results of step (c) to select one or more sub-mixtures for use in conjugation. The process may involve fragmentation of the polysaccharide prior to step (a), or may start with an already-prepared mixture. The fragments may be fragments of the same polysaccharide e.g. of the same serogroup. After step (d), the process may comprise the step of conjugation to a carrier protein, after optional chemical activation.

Prior to conjugation it is usual for a saccharide to be chemically activated in order to introduce a functional group that can react with the carrier. Conditions for saccharide activation can cause hydrolysis, and so it is useful to analyse a saccharide after activation. The term "saccharide" should, where appropriate, be taken to include these activated saccharides. Moreover, the invention provides a process for preparing an activated saccharide for use in preparing a glycoconjugate, comprising the steps of: (a) obtaining a saccharide; (b) chemically activating the saccharide to introduce a functional group that can react with a carrier protein; and (c) analysing the product of step (b) as described herein. The process may include the further step of: (d) reacting the activated saccharide with the carrier protein (which may itself have been activated) to give the glycoconjugate. The process may involve fragmentation of a polysaccharide prior to step (a), or may start with an already-prepared mixture.

The invention can also be used after conjugation. After conjugation, compositions can be analysed using the invention in three ways: first, total saccharides in a composition can be measured e.g. prior to mixing of different conjugates, or prior to release of a vaccine (for regulatory or quality control purposes); second, free unconjugated saccharide in a composition can be measured e.g. to check for incomplete conjugation, or to follow conjugate hydrolysis by monitoring increasing free saccharide over time; third, conjugated saccharide in a composition can be measured, for the same reasons. The first and third ways require the saccharide to be released from the conjugate prior to analysis. To separately assess conjugated and unconjugated saccharides, they must be separated. Free (i.e. unconjugated) saccharide in an aqueous composition can be separated from conjugated saccharide in various ways. The conjugation reaction changes various chemical and physical parameters for the saccharide, and the differences can be exploited for separation. For example, size separation can be used to separate free and conjugated saccharide, as the conjugated material has a higher mass due to the carrier protein. Ultrafiltration is a preferred size separation method. As a further alternative, if conjugates have been adsorbed to an adjuvant then centrifugation will separate adsorbed conjugate (pellet) from free saccharide (supernatant) that desorbs after hydrolysis.

The invention provides a method for analysing a glycoconjugate, comprising the steps of: (a) treating the glycoconjugate to release saccharide from carrier; and (b) analysing the released saccharide as described herein. The invention provides a method for analysing a glycoconjugate composition, comprising the steps of: (a) separating unconjugated saccharide in the composition from conjugated saccharide; and (b) analysing the unconjugated and/or conjugated saccharide as described above.

The invention also provides a method for releasing a vaccine for use by physicians, comprising the steps of: (a) manufacturing a vaccine, including a step of analysis as described herein; and, if the results from step (a) indicate that the vaccine is acceptable for clinical use, (b) releasing the vaccine for use by physicians. Step (a) may be performed on a packaged vaccine, on a bulk vaccine prior to packaging, on saccharides prior to conjugation, etc.

The invention also provides a batch of vaccines, wherein one vaccine within the batch has been analysed using a method of the invention.

General

The term "comprising" encompasses "including" as well as "consisting" e.g. a composition "comprising" X may consist exclusively of X or may include something additional e.g. X+Y. The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

The methods of the invention can be used for analytical and/or preparative purposes. References to "analysing", "analysis", etc. should not be construed as excluding preparative methods.

The degree of polymerisation (DP) of a saccharide is defined as the number of repeating units in that saccharide. For a homopolymer, the SP is thus the same as the number of monosaccharide units. For a heteropolymer, however, the SP is the number of monosaccharide units in the whole chain divided by the number of monosaccharide units in the minimum repeating unit e.g. the DP of $(Glc-Gal)_{10}$ is 10 rather than 20, and the DP of $(Glc-Gal-Neu)_{10}$ is 10 rather than 30.

BRIEF DESCRIPTION OF DRAWINGS

FIG. 2 shows a serial arrangement for the amperometric and spectroscopic detections, whereas

MODES FOR CARRYING OUT THE INVENTION

Ultraviolet Detection of HPAEC Output

Figure 19:
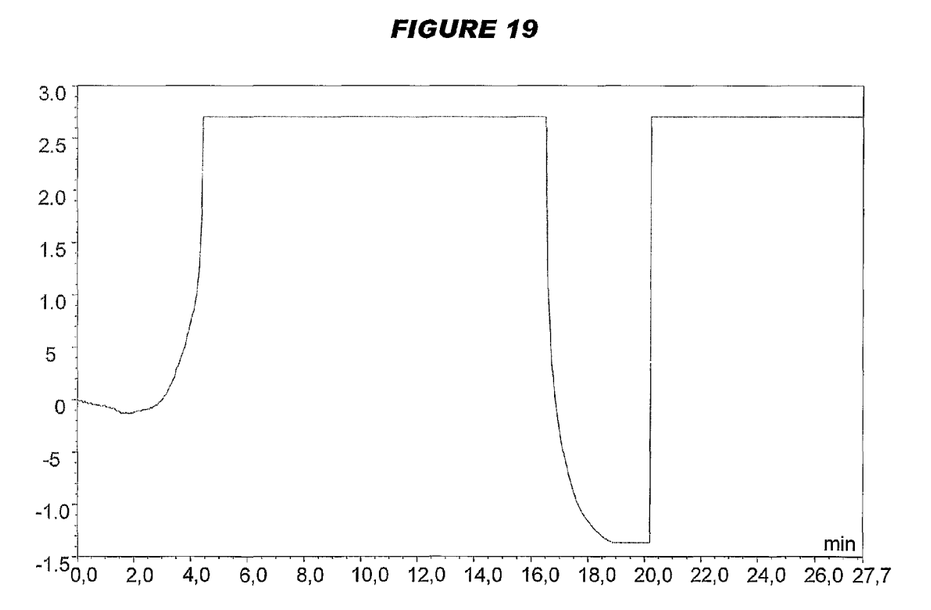
FIG. 19 shows the elution profile of water measured at 214 nm using an acetate/hydroxide and nitrate/hydroxide eluent on a PA1 column, with micromembrane suppression. The elution program was the same as for FIG. 6.

The high pH used during HPAEC analysis of capsular saccharides means that hydroxide ions are present in the eluate, but these ions have high absorbance in the ultraviolet region. As shown in FIG. 19, the use of a standard acetate/hydroxide eluent with just water on a CarboPac PA1 column gives an elution profile in the UV region that will obscure any analyte(s) of interest. In order to add UV detection to analysis of HPAEC eluents, therefore, a different strategy was required.

Combined PAD and UV Analysis of HPAEC Eluent

The capsular saccharide of serogroup A meningococcus was subjected to depolymerisation, to give a pool of charged (phosphate, from mannosamine-1-phosphate monomers) saccharides of mixed length (high DP). Rather than using a PA1 column for HPAEC separation, the mixture was separated on a Dionex IonPac AS11 column with the manufacturer's suggested guard, using a sodium hydroxide gradient as the eluent (flow rate 1.0 ml/min). The eluate from the HPAEC column was analysed in series by electrochemical (PAD, gold electrode) and UV detectors. The output from the integrated amperometric detection is shown in the top profile of FIG. 1, and the output from the UV-visible detection (at 200 nm) is in the bottom profile.

Figure 5:
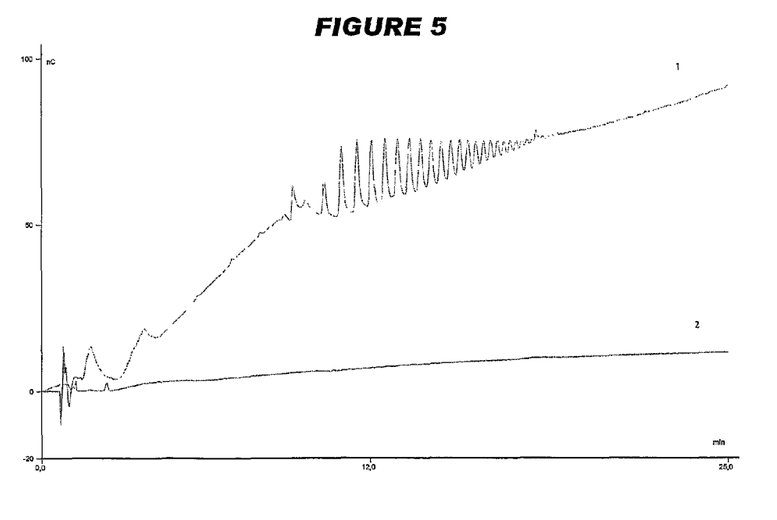
FIG. 5 shows analysis of eluent from a PA1 column, detected by PAD (bottom trace) or by UV (top trace).

The AS11 column has a low capacity (11 µeq). The same analyte was applied to a high capacity Dionex CarboPac PA1 column (100 µeq), and sodium chloride was used as the pushing agent in the eluent. As shown in FIG. 5, the eluent from the PA1 column could not be detected by PAD (bottom trace) but was detectable by UV (top trace). UV detection therefore allows low capacity AEC columns to be used for the analysis of capsular saccharides.

Comparison of Nitrate and Acetate Eluents

Figure 7:
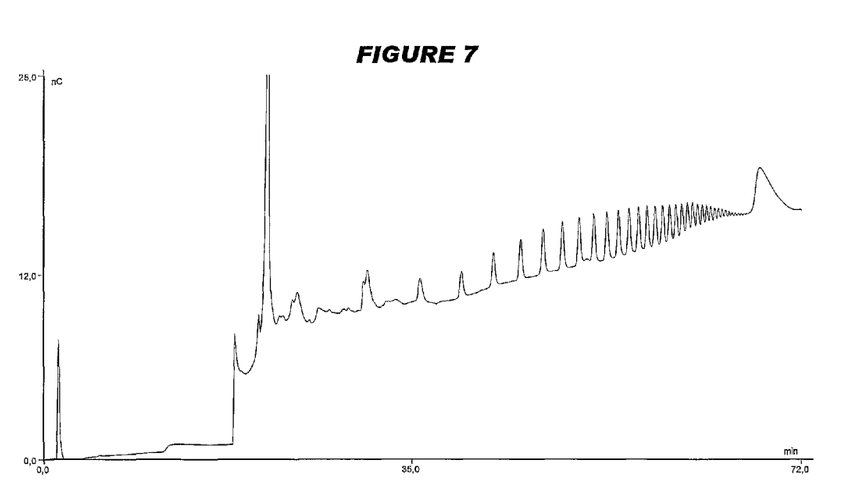
FIGS. 7 and 8 shows eluate analysis of serogroup W135 saccharides on a PA100 column using different eluents.

A pool of oligosaccharide fragments of the capsular saccharide of serogroup W135 meningococcus was analysed by conventional HPAEC-PAD, using a CarboPac PA100 column with a gradient elution using sodium acetate with 100 mM sodium hydroxide. The results are shown in FIG. 7.

Figure 8:
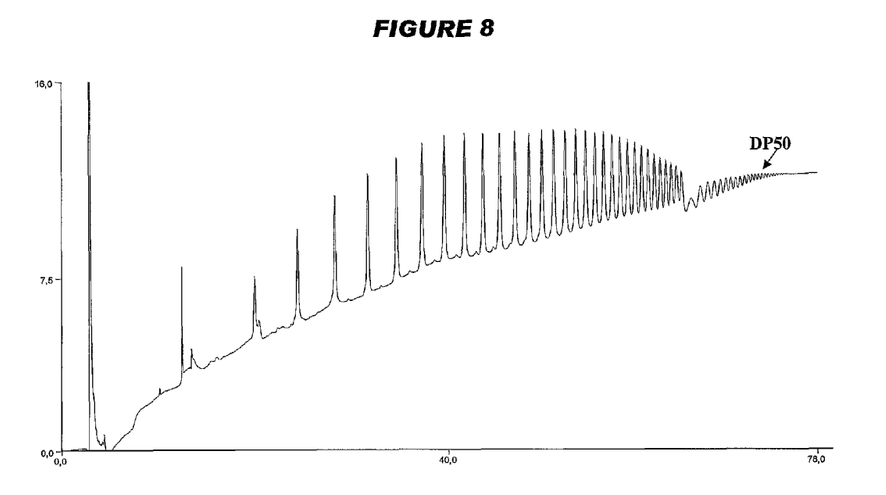

For comparison purposes, the same analysis was performed but with sodium nitrate in the eluent in place of sodium acetate. As shown in FIG. 8, the dynamic range of the output was far greater, and resolution of high DP fragments was better. DP50 fragments could be detected.

Figure 9:
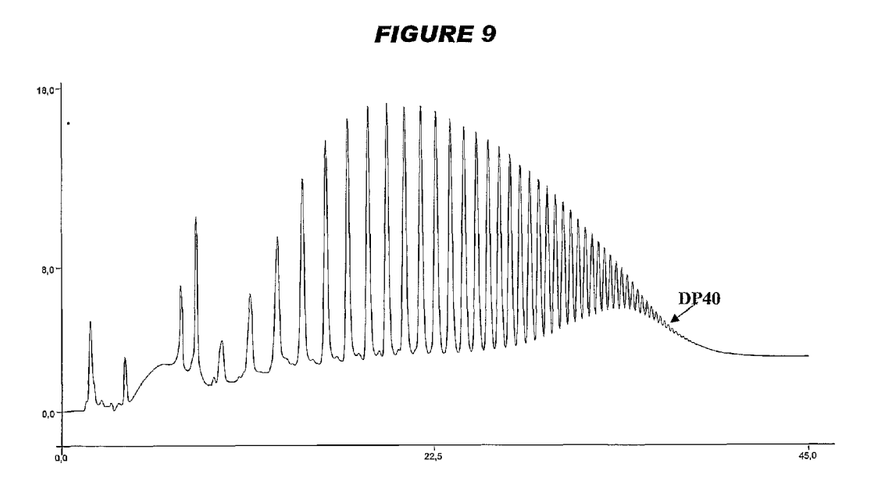
FIG. 9 shows elution of the same analyte on a PA1 column.
Figure 10:
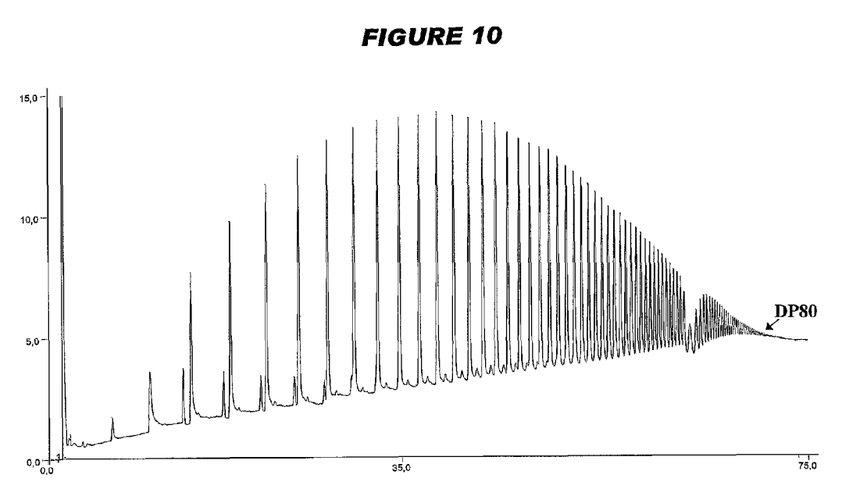
FIG. 10 shows the same analyte on a PA200 column.

Changing to a CarboPac PA1 column increased the dynamic range even further (FIG. 9), and DP40 fragments could be detected. With a 5 µm PA200 column, DP80 fragments could be seen (FIG. 10).

Nitrate salts are therefore useful for eluting capsular saccharides of different lengths from anion exchange columns.

Nitrate Eluent for DP Detection Over Time

The saccharide component of conjugate vaccines can be subject to gradual hydrolysis, and this leads to a reduction in DP over time and to a lower amount of saccharide bound to protein carrier. The depolymerisation of meningococcal serogroup A saccharides under different pH condition was monitored by HPAEC-PAD using a CarboPac PA1 column. The eluent was a mixture of sodium acetate and sodium nitrate in 100 mM sodium hydroxide, with a 1.0 ml/min flow rate.

Three different storage conditions were used: (1) pH ~9 at 37° C. for 4 days; (2) pH ~4 at 37° C. for 4 days; and (3) pH ~7 at −20° C. i.e. recommended storage conditions.

Figure 6:
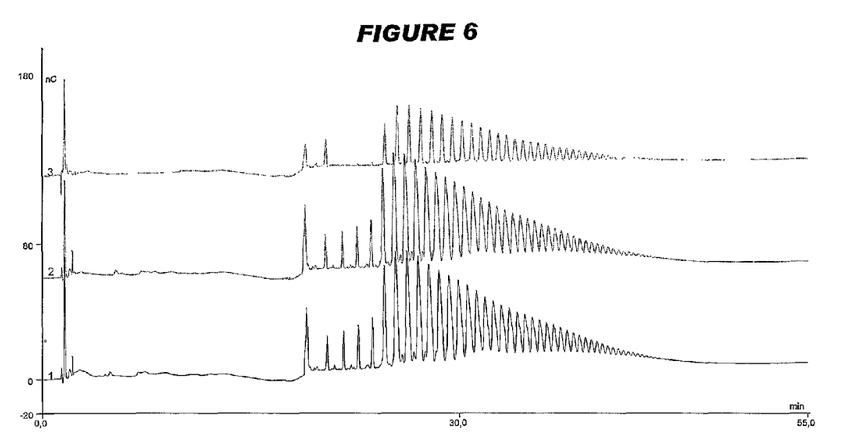
FIG. 6 shows eluate analysis from a PA1 column of a serogroup A sample stored under different conditions. The elution program was the same as for FIG. 19.

As shown in FIG. 6, the addition of nitrate to the eluent allows PAD for the eluate, and low-DP fragments can be detected following depolymerisation. Short fragments are visible for the material stored at 37° C. in positions where no peaks are seen for the material stored below zero (top line).

*H. influenzae* Analysis with Low Capacity Column

A pool of Hib oligosaccharides (DP 2 to 6) was analysed by conventional HPAEC-PAD on a CarboPac PA100 column. The eluent was a 30 mM to 100 mM sodium acetate gradient with 100 mM NaOH, over 24 minutes at a 0.8 ml/min flow rate. The results are in FIG. 11.

Figure 11:
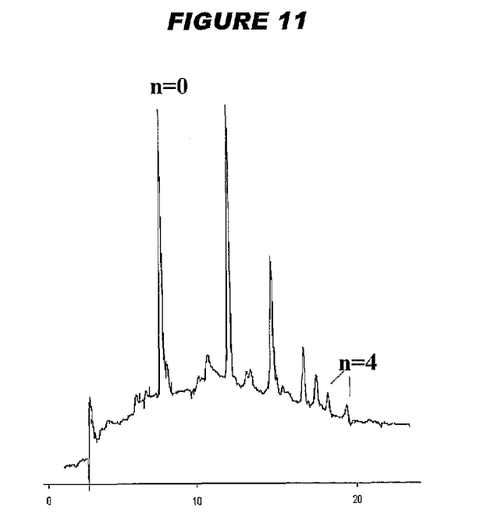
FIG. 11 shows eluate analysis of Hib oligosaccharides on a PA100 column.

Only short chain oligomers eluted from the CarboPac PA-100, and elution required a high percentage of sodium acetate as a pushing agent. Even then, the DP5 and DP6 oligomers were poorly resolved and with low sensitivity. The CarboPac PA-100 is thus not suitable for profiling of a pool of Hib oligosaccharides with DP>4. Consequently a different chromatographic column was investigated.

Figure 12:
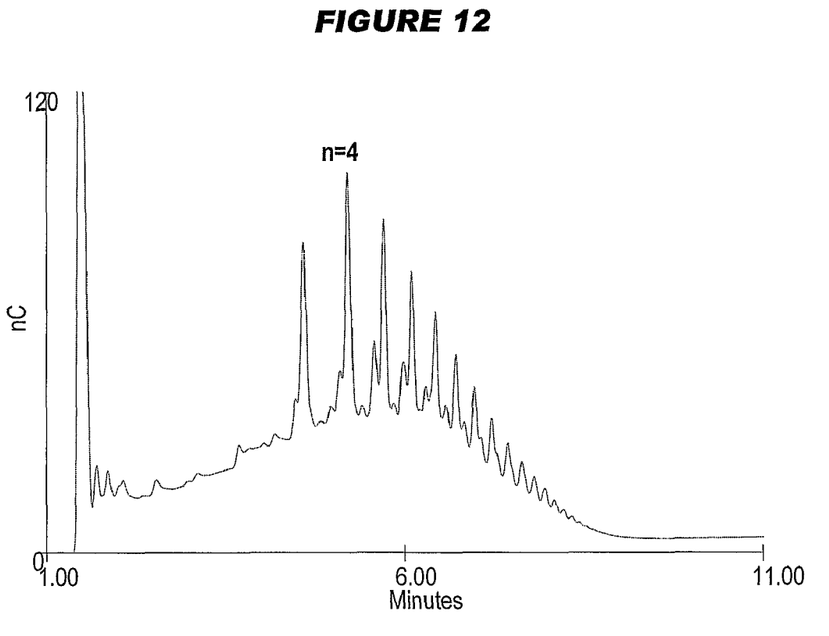
FIG. 12 shows eluate analysis of a pool of hydrolysed Hib saccharide on a AS11 column.

An IonPac AS11 column was used to analyse a pool of hydrolysed Hib saccharide with an average DP of 12.44. This column has a high hydroxide selectivity, thus permitting elution of highly charged anions at lower hydroxide concentrations than previously used for strongly retained polyanions (e.g. the Hib fragments). The eluent was 3 mM to 150 mM NaOH over 15 minutes. The results are in FIG. 12, again showing that low capacity columns can be used for analysing bacterial capsular saccharides. The elution was very fast and needed only a hydroxide gradient. All components from the Hib pool could be resolved in a chromatographic run lasting less than 10 minutes.

Meningococcal Serogroup A Saccharide with Low Capacity Column

Figure 13:
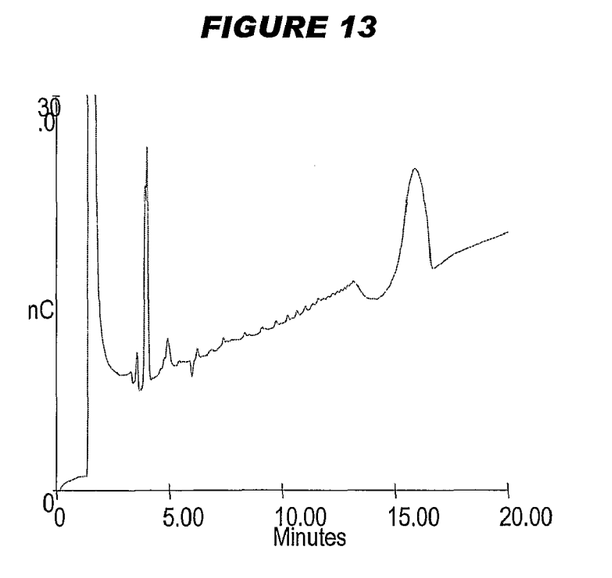
FIG. 13 shows eluate analysis of a serogroup A polysaccharide on a AS11 column. The same analysis after hydrolysis of the saccharide is shown in FIG. 14

The IonPac AS11 column was used to analyse the molecular weight distribution of the serogroup A meningococcal capsular polysaccharide. FIG. 13 shows a chromatogram obtained for a sample of the polysaccharide with a DP of ~200, using a hydroxide gradient of 10 to 150 mM in 19 minutes. Surprisingly, the column was able to separate this high MW polyanion, and the column efficiency is so high that the analyte eluted in just 17 minutes in a relatively narrow peak. This result is much superior to methods such as gel permeation chromatography.

Figure 14:
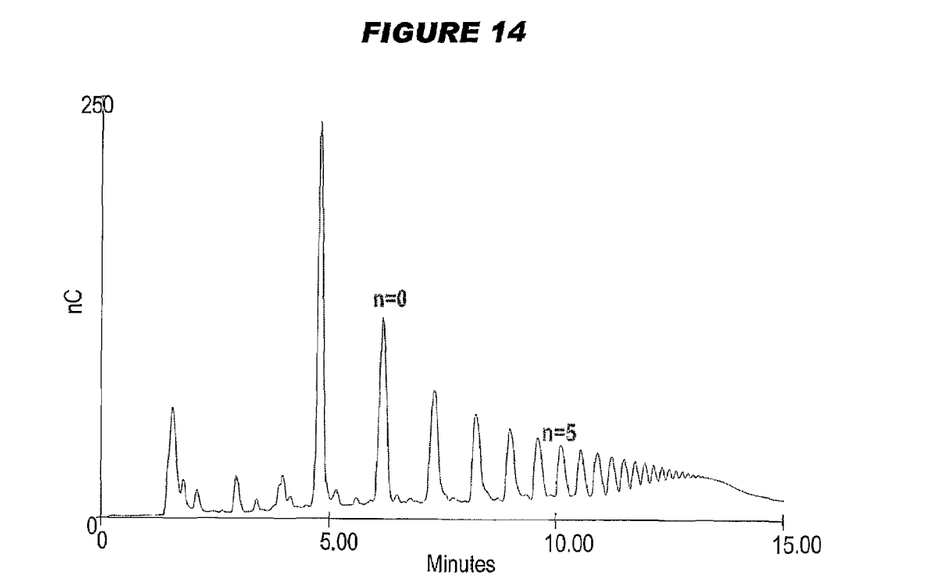

The same column was used to profile the oligosaccharides obtained after acid hydrolysis of the polysaccharide. As shown in FIG. 14, oligosaccharides of increasing DP could be resolved, with a correlation between DP and retention time on HPAEC-PAD.

Meningococcal Serogroup C Saccharide with Low Capacity Column

The serogroup C polysaccharide is a homopolymer of $\alpha$-2, 9-linked N-acetyl-neuraminic acids, which is partially O-acetylated. It is thus a polycarboxylate anion. The chromatographic pattern of the serogroup C saccharide is complicated by the presence of the O-acetyl groups, as each oligomer gives rise to a number of peaks depending on the distribution of acetyl groups in the structure.

Figure 15:
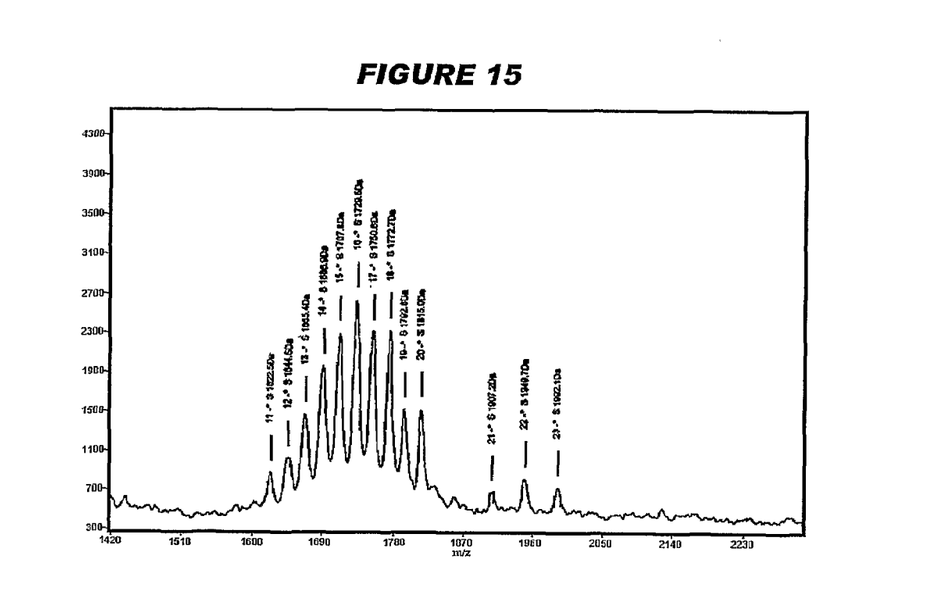
FIG. 15 shows MALDI-TOF mass spectrometry of a serogroup C standard.
Figure 16:
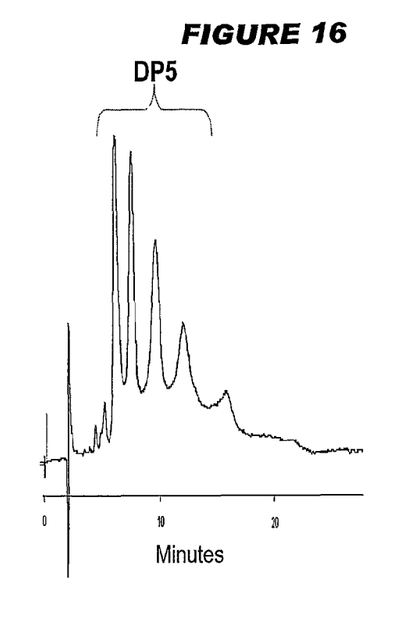
FIG. 16 shows eluate analysis of the same standard on a PA1 column. The standard was also analysed by a AS11 column, as shown in FIG. 17.

A purified DP5 standard was analysed by MALDI-TOF mass spectrometry, and was seen to contain a distribution of multiple different oligomers (FIG. 15). Analysis of the same standard by HPAEC-PAD on a CarboPac PA1 column is shown in FIG. 16. Elution from the column required strong conditions (500 mM sodium acetate, 100 mM sodium hydroxide), and the differences between FIGS. 15 and 16 show that this acetate treatment alters the natural distribution of acetyl groups in the saccharide. The use of strong high capacity AEC columns for analysing acetylated saccharides is therefore not optimal.

Figure 17:
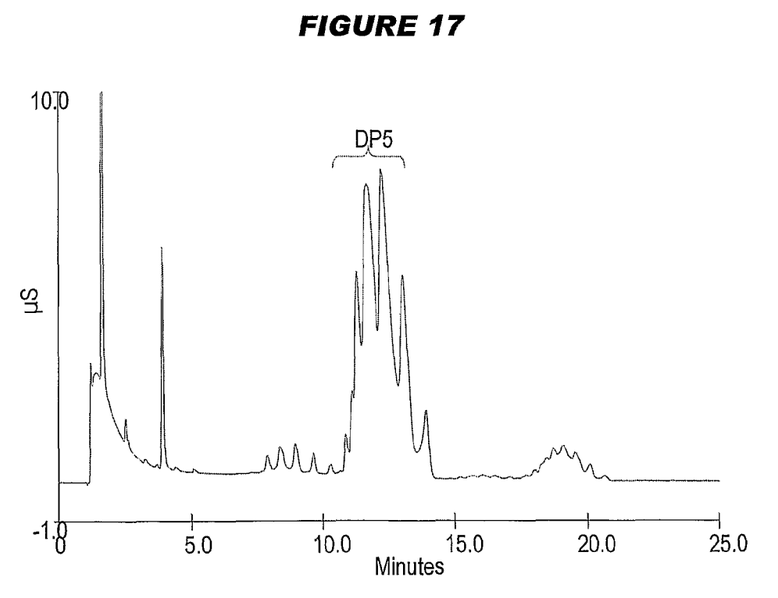

An IonPac AS11 column coupled with suppressed conductivity detection was therefore used instead. As shown in FIG. 17, using a 10 mM to 60 mM sodium hydroxide gradient (no acetate) it was possible to elute the DP5 standard with a profile showing the different oligosaccharides and the distribution of O-acetyl groups. Interpretation of the chromatographic pattern is much simpler than for the MALDI-TOF pattern, which is complicated by the presence of different amounts of sodium as counter-ion which has a molecular weight equal to half the acetyl group weight.

Figure 18:
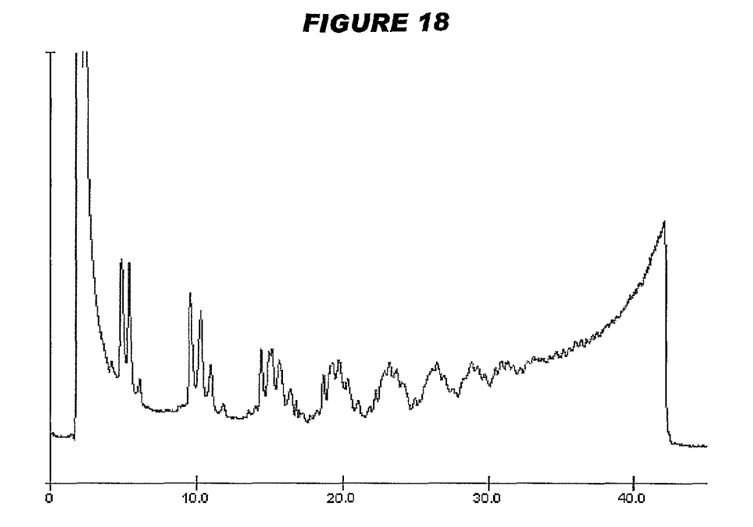
FIG. 18 shows analysis of a hydrolysed serogroup C polysaccharide on a AS111 column.

The elution pattern seen for the DP5 standard was also seen repeated at different lengths for the hydrolysis product of the capsular polysaccharide (FIG. 18).

It will be understood that the invention has been described by way of example only and modifications may be made whilst remaining within the scope and spirit of the invention.

REFERENCES

The Contents of which are Hereby Incorporated by Reference

[1] *Vaccines* (eds. Plotkin et al.) 4th edition, ISBN: 0721696880.
[2] Hardy et al. (1988) *Anal Biochem* 170:54-62.
[3] Wang et al. (1990) *Anal Biochem* 190:182-187.
[4] Mellor et al. (2000) *Anal Biochem* 284:136-142.
[5] *Product Manual* for IonPac™ AS11 column. Dionex™ document 034791, revision 08.
[6] Gert-Jan et al. (2002) *J Biol Chem* 277:25929-25936.
[7] LaCourse & Johnson (1993) *Anal Chem* 65:50-55.
[8] Jones (2001) *Curr Opin Investig Drugs* 2:47-49.

The invention claimed is:

1. A method for detecting the presence of a capsular polysaccharide or a capsular oligosaccharide analyte in a sample, comprising the steps of: (a) applying the sample to an anion exchange chromatography column, such that analyte in the sample binds to the column; (b) eluting the analyte from the column using an eluent comprising an anion selected from the group consisting of a nitrate, a chloride, a carbonate and a borate; and (c) analyzing the eluate by both (i) amperometry and (ii) ultraviolet (UV) absorption spectroscopy and/or visible light absorption spectroscopy.

2. The method of claim 1, wherein the method uses a hydroxide-selective anion exchange chromatography column.

3. The method of claim 1, wherein the anion exchange chromatography column is a high performance anion exchange chromatography (HPAEC) column.

4. The method of claim 1, wherein pulsed amperometric detection (PAD) is used.

5. The method of claim 1, wherein the eluate comprises a bacterial capsular polysaccharide, a capsular oligosaccharide, or a saccharide-containing fragment of a bacterial capsular polysaccharide.

6. The method of claim 5, wherein the bacterial capsular polysaccharide or the capsular oligosaccharide is from *Neisseria meningitidis, Streptococcus pneumoniae, Streptococcus agalactiae, Pseudomonas aeruginosa* or *Staphylococcus aureus*.

7. The method of claim 1, wherein the chromatography is performed using a column that has a capacity of less than 50 µeq.

8. The method of claim 3, wherein pulsed amperometric detection (PAD) is used.

9. The method of claim 3, wherein the eluate comprises a bacterial capsular polysaccharide, a capsular oligosaccharide, or a saccharide-containing fragment of a bacterial capsular polysaccharide.

10. The method of claim 9, wherein the bacterial capsular polysaccharide or the capsular oligosaccharide is from *Neisseria meningitidis, Streptococcus pneumoniae, Streptococcus agalactiae, Pseudomonas aeruginosa* or *Staphylococcus aureus*.

* * * * *